Figure 1:
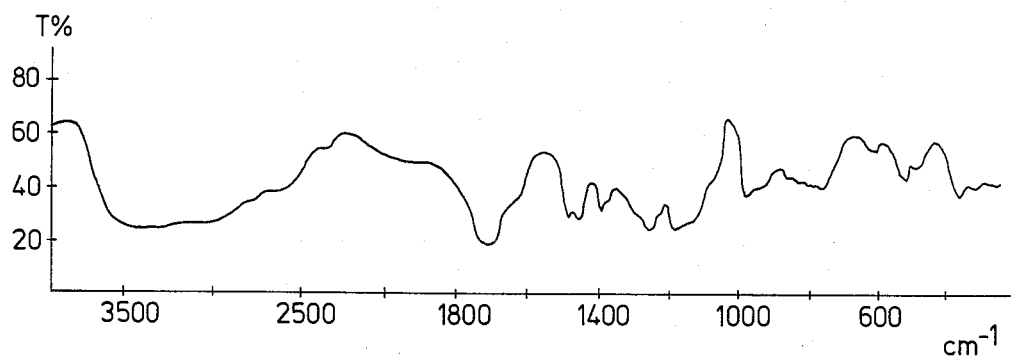

United States Patent [19]

Orbán et al.

[11] Patent Number: 4,539,199
[45] Date of Patent: Sep. 3, 1985

[54] SUSTAINED RELEASE PHARMACEUTICAL COMPOSITIONS

[75] Inventors: Ernö Orbán; János Borvendég; László Nagy; Márta Sótinée Tolvay; Erzsébet Bander, all of Budapest, Hungary

[73] Assignee: Egyt Gyogyszervegyeszeti Gyar, Budapest, Hungary

[21] Appl. No.: 384,084

[22] Filed: Jun. 1, 1982

Related U.S. Application Data

[63] Continuation-in-part of Ser. No. 224,961, Jan. 14, 1981, abandoned.

[51] Int. Cl.$^3$ ............... A01N 25/12; A61K 31/78
[52] U.S. Cl. ........................... 424/22; 424/81
[58] Field of Search ..................... 424/81, 22

[56] References Cited

U.S. PATENT DOCUMENTS

| 3,390,050 | 6/1968 | Speiser | 424/81 |
| 3,576,760 | 4/1971 | Gould et al. | 424/81 |
| 3,629,392 | 12/1971 | Banker et al. | 424/81 |
| 3,679,653 | 7/1972 | Schuck et al. | 424/81 |
| 3,764,477 | 10/1973 | Lehmann et al. | 424/81 |
| 3,904,745 | 9/1975 | Cohen et al. | 424/81 |
| 4,248,855 | 2/1981 | Blank et al. | 424/19 |

FOREIGN PATENT DOCUMENTS

| 2636559 | 3/1977 | Fed. Rep. of Germany | 424/81 |
| 2712609 | 9/1977 | Fed. Rep. of Germany | 424/81 |
| 7211055 | 2/1973 | Netherlands | 424/81 |
| 1563390 | 3/1980 | United Kingdom | 424/81 |

OTHER PUBLICATIONS

Merck Index, 9th Ed., p. 2054.

*Primary Examiner*—Delbert R. Phillips
*Assistant Examiner*—F. Moezie
*Attorney, Agent, or Firm*—Young & Thompson

[57] ABSTRACT

Pharmaceutical compositions for sustained release of pharmaceutical compounds comprising a reaction product of a water soluble salt of a pharmaceutically active compound containing a primary, secondary or tertiary amino group, and an alkali or ammonium salt of a synthetic copolymer containing an acid group, and selected from the group consisting of methacrylic acid/methacrylic acid methyl ester, methacrylic acid/acrylic acid methyl ester and methacrylic acid/acrylic acid methyl ester/methacrylic acid methyl ester copolymers and a pharmaceutically acceptable excipient. The water soluble salt of a pharmaceutically active compound containing a primary, secondary or tertiary amino group is reacted in aqueous medium with an alkali or ammonium salt of a copolymer selected from the group consisting of the above mentioned copolymers, and the resulting product is converted into a pharmaceutical composition.

7 Claims, 5 Drawing Figures

SUSTAINED RELEASE PHARMACEUTICAL COMPOSITIONS

This application is a continuation-in-part of our copending application Ser. No. 224,961 filed on Jan. 14, 1981 and now abandoned.

The invention relates to novel sustained release pharmaceutical compositions which may be advantageously applied in human therapy.

The main advantage of sustained release pharmaceutical compositions is as follows: only a single medication is required daily, the treatment of pathological conditions requiring regular injections can be simplified, and the effects of the active agent (such as hypnotic) can be well controlled over the complete night period.

Several methods are known for the preparation of sustained release compositions the most important being the following:

1. Preparation of a combined composition which also contains, beside the active agent, a component decreasing physiological absorption, such as adrenaline.
2. Suppression of the dissolution of the active agent by physical means. Compositions of this type include solid drugs provided with various film coatings, furthermore drugs incorporated into materials hardly soluble or insoluble in the gastrointestinal tract.
3. Chemical conversion of the pharmaceutically active molecule, i.e. preparation of poorly soluble salts, esters, ethers, complexes or addition compounds.

The compositions of the present invention are prepared according to any of the methods listed in the 3rd group.

The disadvantage of method 1 is that the absorption conditions of orally administered drugs cannot be influenced in this way. The applicability of this method is rather limited even in the case of parenteral administration.

Of the procedures listed above group 2 has the widest scope of applicability. As methacrylic acid containing copolymers are frequently used both for film coating and entrapping some representative examples are listed as follows: In U.S. Pat. No. 3,390,050 vinyl acetate/crotonic acid and acrylic acid ethyl ester/t-butyl acrylamide/acrylic acid copolymers are reacted with methacrylic acid or methacrylic acid methyl ester monomers. In the course of the ensuing polymerization the dissolved or suspended active agent is physically entrapped in the copolymer formed. The physical entrapping is confirmed by the fact that in Examples 2, 5 and 6 the active agent is not even dissolved. In the procedure described in U.S. Pat. No. 3,576,760 the copolymers formed from acrylic acid hydroxyethyl ester, methacrylic acid hydroxyethyl ester, and related compounds, and methacrylic acid are used for entrapping (the title of the patent: "Water soluble entrapping").

The procedure described in U.S. Pat. No. 3,629,392 is based on the coagulation of polymer latexes in the course of which the dissolved active agent is adsorbed physico-chemically by the large surface polymer particles. This adsorptive property of polymers is well known in the literature [J. Autian, J. Pharm. Sci., 52, 105–122 (1963)]. Coagulation is usually induced with the salts of the active compounds or eventually with inorganic salts or alcohols. In some cases both the cation and the anion of the drug are bound by the polymer particles though no equivalent amounts of the reacting components are required.

Netherland Pat. No. 7,211,055 describes the preparation of controlled release dispersions consisting of acrylate/methacrylate copolymers. According to the procedure of the invention the macromolecular material is partially neutralized (NaOH, zinc-, ammonium- or cupriammonium compounds) prior to its admixture with the active ingredient. Neutralization is always carried out with the purpose of converting the water insoluble copolymers into water soluble Na, Zn or Cu salts which may be applied either for physical stabilization or for film coating from the dispersions formed, containing the active agent. However, there are no active groups (i.e. amino groups suitable for salt formation) in either of the biologically active compounds of the Examples which would enable any chemical interaction with the copolymers. Consequently even theoretically there is no possibility of any salt formation between the macromolecules and the active ingredients.

The major part of the copolymers of the German published application No. 2,712,609 is devoid of any functional group which could interact chemically with the drug molecules, the commercially available Carbopol, being an acrylic acid polymer, is applied only for the physical stabilization of the solid particles in some dispersions. The addition of sodium hydroxide to the dispersion aims to enhance the stabilizing effect of Carbopol by increasing the solubility of the macromolecular substance in the dispersion medium through the —COONa groups of polyacrylic acid, formed in the course of neutralization.

In U.S. Pat. No. 4,248,855, sustained release pharmaceutical compositions are prepared by mixing the solutions of drug bases in an organic solvent or aqueous solutions of the drug salts with the solution of methacrylates in an organic solvent or with a dispersion prepared from these solutions. The authors assume that in this procedure a salt is formed between the drug molecule and the polymethacrylates. On the basis of theoretical and practical studies carried out with method available to those skilled in the art it can be stated, however, that no salt can be formed at these conditions, and the declared results of the procedure fail to be reproducible. Theoretically the salt bond —COO$^-$=N$^+$= between the drug molecules and the polymer can only be formed if both molecules are in a dissociated state at the moment of interaction. However, as in the procedure the copolymer is always used in an organic solvent solution or dispersion the copolymer fails to dissociate due to the organic solvent; consequently, the system is devoid of the prerequisites of salt formation.

This theoretical presumption is confirmed by the IR spectroscopic study of the structure of the composition prepared according to both Examples 1 and 2 of the anterior Patent and our own method, by using an identical drug (Pilocarpin) in both cases. At the salt formation of the drug molecules containing basic moieties and of acrylate copolymers the —COOH groups of the copolymer are transformed into —COO$^-$=N$^+$= groups. This process may be monitored through the $\gamma$COO$^-$ band appearing in the IR spectrum of the product formed (K. Nakanishi, Infrared Absorption Spectroscopy, p. 44, Holden-Day Inc., San Francisco, 1962).

In the original copolymer only —COOCH$_3$ and —COOH groups are present with valence bands between 1700 and 1750 cm$^{-1}$. The $\gamma$COO$^-$ band, signalling the presence of a salt, appears in the range of 1610 to 1550 cm$^{-1}$ in the IR spectrum while the spectrum of the intact copolymer is devoid of any such band in this range. In the IR spectrum of the product prepared according to our process there appears a definite band at 1660 cm$^{-1}$, indicating the presence of carboxylate ions, which in the IR spectrum of the products prepared according to Examples 1 and 2 of the cited patent applications there is only a slight deviation from that of the copolymer itself.

The comparison of spectra permits one to draw the definite conclusion that the IR spectrum of the composition prepared according to the anterior patent application is a superposition of the IR spectra of Pilocarpin base and the copolymer.

All the above listed, patented procedures ensure the sustained release of biologically active drugs by creating physical and not chemical interaction between the drug molecules and the matrix (all these methods may be ranged into Group 2).

The chemical methods listed in Group 3 are the most up to date ones. Pharmaceutical compositions prepared with these methods ensure the sustained release of the active agent at molecular level.

The inventors of U.S. Pat. Nos. 3,679,653 and 3,764,477 succeeded in binding peptide type molecules to polymers by forming a covalent bond. The inventors of U.S. Pat. No. 3,904,745 polymerized the monoester of acrylic acid or methacrylic acid with a sulfur-containing compound, i.e. vinyl-propanesulfonic acid. The resin-matrix obtained was used for the binding of chlorophenylramine maleate furnishing drug-resinates.

The invention aims at providing a novel process which eliminates the disadvantages of the known ones and enables one to produce tasteless pharmaceutical compositions with prolonged effects in a simple and easily performed way.

The invention is based on the recognition that when a water soluble salt of a pharmaceutically active compound containing a primary, secondary or tertiary amino group formed with a mineral or organic acid (such as hydrochloric, hydrobromic, sulfuric, phosphoric, nitric, acetic, tartric, citric, fumaric or maleic acid) is reacted in aqueous medium with a water soluble salt, such as sodium, potassium, or ammonium salt of a copolymer containing methacrylic acid, the carboxy groups of the copolymer form salts with the pharmaceutically active free molecule, and the resulting salts can be used to great advantage as drugs with prolonged effects. The term "methacrylate" used in the specification and claims refers to a partial ester of methacrylic acid.

When the pharmaceutically active molecule contains a primary amino group, the following reactions take place:

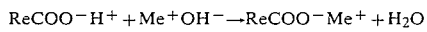

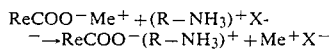

In the above equations
ReCOO$^-$H$^+$ is the copolymer,
(R—NH$_3$)$^+$ is a cation formed from the biologically active molecule,
Me$^+$ is an alkali metal (such as sodium, potassium) or ammonium-ion, and
X$^-$ is an organic or inorganic anion (such as Cl$^-$, CH$_3$COO$^-$, etc.).

The resulting drug salts have different water solubilities. The actual degree of solubility depends mainly on the water solubility of the free base, but the number of the carboxy groups in the polymer which react with the base also influences the solubility of the end product.

According to our experiences a stoichiometric reaction takes place when the molecules of pharmaceutically active compound, containing a primary, secondary or tertiary basic nitrogen atom or containing a heterocycle with a basic nitrogen atom are involved in the above process.

On the basis of the prior art it was not foreseen that polymethacrylic acid/polymethacrylate copolymers can be reacted with certain drug molecules to obtain a product with a prolonged effect.

Based on the above, the invention relates to a process for the preparation of sustained release pharmaceutical compositions comprising an active agent having a basic nitrogen atom, and using a methacrylic acid containing copolymer. The process of the invention is characterized in that a water soluble salt of a pharmaceutically active agent containing a primary, secondary, or tertiary amino group is reacted with stoichiometric amounts of a sodium, potassium or ammonium salt of the methacrylic acid/methacrylic acid methyl ester or methacrylic acid/acrylic acid methyl ester or methacrylic acid/acrylic acid methyl ester/methacrylic acid methyl ester copolymer dissolved in water.

The reaction can also be carried out by dispersing microcrystalline cellulose in the aqueous solution of the copolymer prior to the reaction. The resulting [drug$^+$]-[copolymer$^-$] salt is converted—by using known pharmaceutical vehicles—into suspensions, capsules or any other pharmaceutical formulations.

According to a preferred method of the invention the drug-copolymer salt reaction is carried out by dissolving the sodium, potassium or ammonium salt of the copolymer in water and adding the aqueous solution of the drug-base salt while stirring. The drug-polymethacrylate salt formed is separated from the reaction mixture by filtration and is converted by means of granulation and subsequent drying into a granulate suitable for further processing.

It is advantageous to apply as copolymer components methacrylic acid/methacrylic acid methyl ester 1:1 copolymers, preferably the commercially available solid copolymers of the firm Röhm Pharma (Weiterstadt, FRG), registered as Eudragit L preparations: Eudragit L 100 and Eudragit L 90 or an aqueous dispersion containing 30 percent of the copolymer designated as Eudragit L 30 D or methacrylic acid/acrylic acid methyl ester 1:1 copolymers, preferably the solid commercial preparation MPM-05 of the firm Tanabe Seiyaku (Osaka, Japan) or methacrylic acid/acrylic acid methyl ester/methacrylic acid methyl ester 1:1:1 molar copolymerizate, preferably the solid commercial preparation MPM-06 of the firm Tanabe Seiyaku (Osaka, Japan). Any other copolymer preparations of different firms containing free carboxy groups may naturally also be used for the forming of drug-polymethacrylate salts.

The reaction according to the patent application can be carried out at room temperature under very simple conditions. After being the reactants into contact with each other, the reaction proceeds immediately, with appropriate stirring. In the production of relatively large batches, it is preferable to stir the mixture for 1 to 1.5 hours after combining the reactants, and to separate the product only after this stirring period.

The reaction can be applied to a wide variety of biologically active molecules containing primary, secondary or tertiary amino groups, since the biologically active free bases, generally poorly soluble in water, can easily be converted into water soluble salts (such as hydrochlorides, sulfates, acetates, etc.). Thus the drug-copolymer salts can be prepared economically even in large-scale production.

The process according to the patent application provides novel drug-copolymer compounds with well-defined structures. In these compounds a carboxylate-ammonium salt bond is formed between the carboxy groups of the acid and the basic nitrogen atoms of the drug. The formation of the carboxylate-ammonium structure is proved by the IR spectra.

IR spectroscopy is a suitable method for the qualitative detection of salt formation between the methacrylic acid-methacrylate copolymer and the organic base. The spectra can be recorded in solid state (KBr pellets) without dissolving the substance; thus dissociation effects appearing as a consequence of dissolution can be eliminated.

Figure 2:
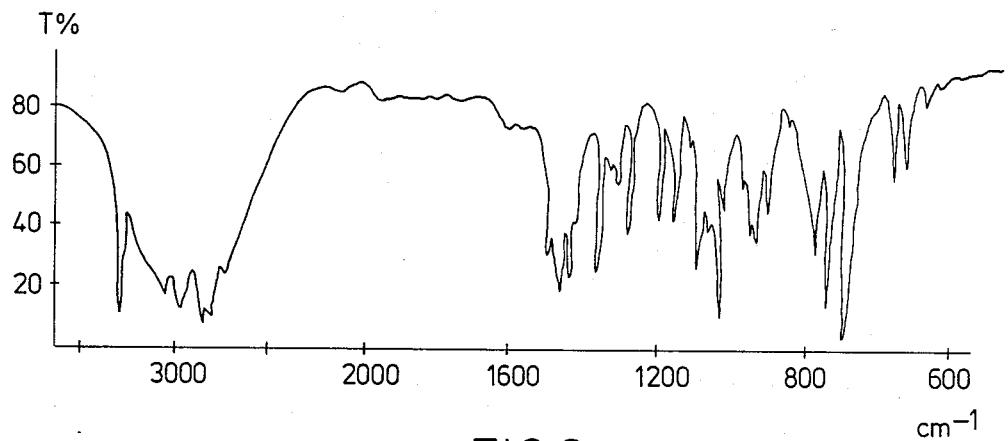
Figure 3:
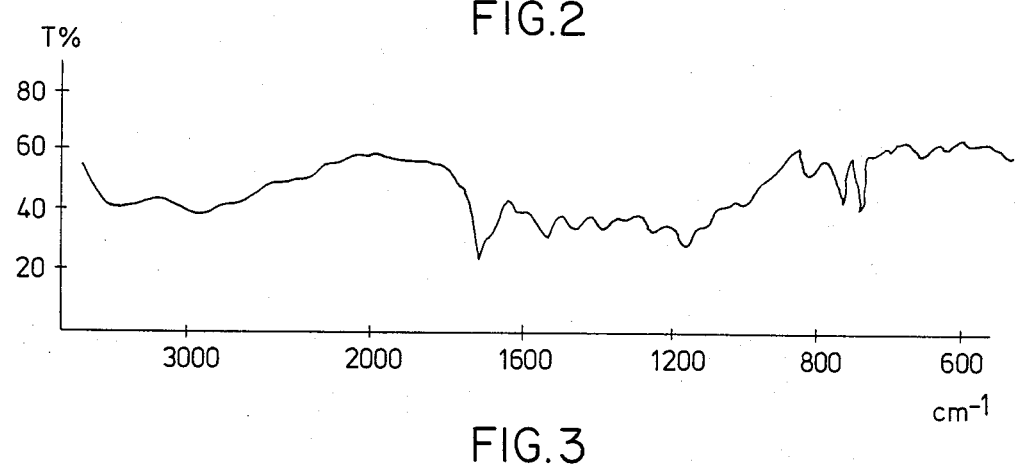
Figure 4:
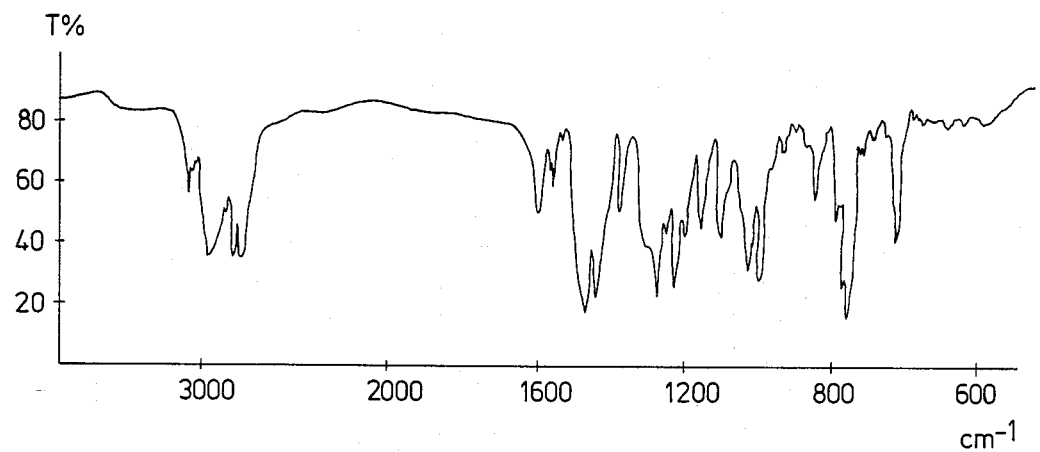
Figure 5:
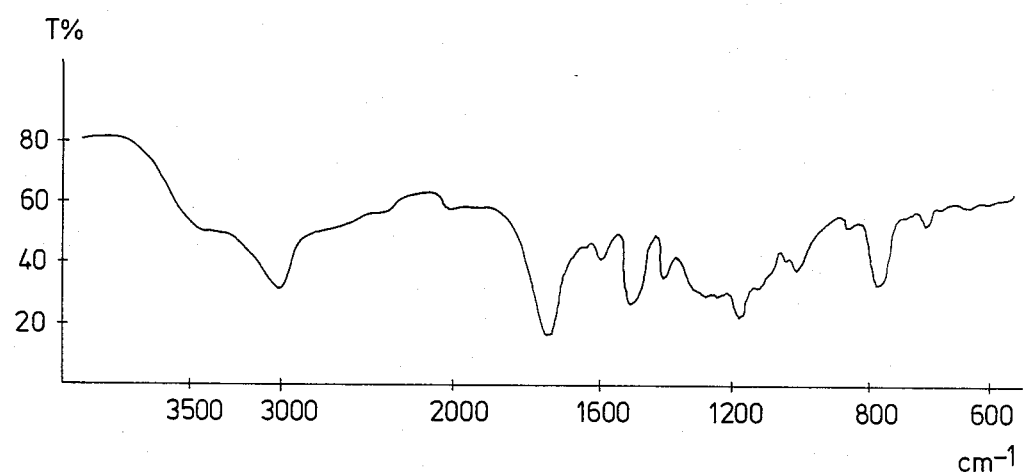

The IR spectrum of the methacrylic acid/methacrylic acid methyl ester (1:1) copolymer is shown in FIG. 1. The IR spectra of the free bases investigated and the drug-copolymer salts prepared therefrom were also recorded. Four of these spectra are shown in FIGS. 2 to 5. FIG. 2 is a spectrum of ephedrine(beta-phenyl-propanol-methylamine) base. FIG. 3 is the spectrum of the ephendrine salt of methacrylic acid/methacrylic acid methylester (1:1) copolymer, FIG. 4 is the spectrum of doxepine [11-/3-dimethylamino-propylidene/-6,11-dihydro-dibenzo/b,e/oxepine/] base, whereas FIG. 5 is the spectrum of the doxepine salt of the methacrylic acid/methacrylic acid methyl ester (1:1) copolymer.

The spectra show the following main features:

1. In the spectrum of the methacrylic acid-methacrylate copolymer the γCO bands of the ester and of the carboxylic acid are overlapping (1730 to 1680 cm$^{-1}$). Such a band does not appear in the spectra of the salts, since the carbonyl group of the carboxylic acid disappears and the bands of the resulting carboxylate ion appear in another region of the spectrum.

2. The $\gamma_{as}CO_2^-$ band of carboxylate ions appears at 1500–1600 cm$^{-1}$ as in the spectra of the copolymer salts. There is no absorption in this region in the spectrum of the free copolymer.

3. The strong and sharp γNH band appearing in the spectrum of ephedrine disappears upon salt formation, being replaced by an N$^+$H$_2$ band at lower frequencies.

The main advantages of the process of the invention are as follows:

a. The drug copolymer salt decomposes to its constituents in the gastrointestinal tract where the biologically active molecule is liberated as a free base or as its hydrochloride which is readily absorbed from the gastrointestinal tract.

b. The salt character of the compound obtained in the process of the invention ensures a proper stability for the original drug.

c. The copolymer utilized is completely indifferent physiologically. Its use in orally applicable medicines has a tradition of several years. According to the literature (H. P. Fiedler: Lexikon der Hilfstoffe für Pharmazie, Kosmetik und angrenzende Gebiete, p. 202, Aulendorf, Württenberg, 1971) the copolymer is not absorbed from the gastrointestinal tract, it is eliminated with the feces in unchanged form.

The composition of drug-copolymer salts prepared according to the following Examples is summarized in Table 1.

TABLE 1

| | | Composition of the reaction product | |
|---|---|---|---|
| Example No | Reaction product | Pharmacologically active component (w/w %) | Copolymer (w/w %) |
| 1 | Ephedrine[poly(methacrylic acid/methacrylic acid methyl ester)] | 24.3 | 75.7 |
| 2 | Doxepine[poly(methacrylic acid/methacrylic acid methyl ester)] | 36.5 | 63.5 |
| 3 | Chloropromazine[poly(methacrylic acid/acrylic acid methyl ester)] | 39.9 | 60.1 |
| 4 | Trimipramine[poly(methacrylic acid/acrylic acid methyl ester/methacrylic acid methyl ester)] | 32.9 | 67.1 |
| 5 | Quinidine[poly(methacrylic acid/methacrylic acid methyl ester)] | 48.0 | 52.0 |
| 6 | Bencyclane[poly(methacrylic acid/methacrylic acid methyl ester)] | 29.3 | 70.7 |
| 7 | Papaverine[poly(methacrylic acid/methacrylic acid methyl ester)] | 43.5 | 56.5 |
| 8 | Cloranolol[poly(methacrylic acid/methacrylic acid methyl ester)] | 32.1 | 67.9 |

The following Examples are illustrative of the invention without limiting it.

EXAMPLE 1

Preparation of a sustained release suspension containing ephedrine 100 g of ephedrine(beta-phenyl-propanol-methylamine hydrochloride) (USP XX) is dissolved in 0.9 liter of deionized water and the resulting solution added at constant stirring to a sodium-polymethacrylate solution of the following composition:

Aqueous copolymer dispersion containing 6 percent (w/w) of Eudragit L 30 D . . . 5,100 g 5 percent (w/v) aqueous sodium hydroxide solution . . . 396 ml The resulting precipitate is left to settle for 30 minutes then is filtered with reduced pressure, washed with 1 liter of deionized water and repeatedly filtered. The resulting material is granulated on a sieve (14 mesh, ASTM) and dried at room temperature. The dry granulate is ground to a fine powder (400/450 mesh). 17.7 g of this fine powder is dispersed in a mixture containing 20 g of Orange Syrup (U.S.N.F. XV), 0.5 g of methyl cellulose (USP XX), 0.1 g of Methylparaben (U.S.N.F. XV) and 62 ml of distilled water.

5 ml of the suspension prepared contains ephedrine-polymethacrylate corresponding to 150 mg of ephedrine base.

EXAMPLE 2

Preparation of sustained release capsules containing doxepine 100 g of doxepine hydrochloride [11-(3-dimethylamine-propylidene)-6,11-dihydro-dibenzo[b,e]-oxepine hydrochloride) (Remington's Pharmaceutical Sciences XIV Ed.) is dissolved in 1.5 liters of deionized water and added at constant stirring to a solution of sodium-polymethacrylate of the following composition:

Aqueous copolymer dispersion containing 6 percent (w/w) of Eudragit L 30 D . . . 2570 g
5 percent (w/v) aqueous sodium hydroxide solution . . . 224 ml The resulting precipitate is separated, filtered, washed according to Example 1, and is granulated on a 14 mesh sieve. The granulate is dried at reduced pressure at 35° C. for 20 hours. The dry material is regranulated on a 25 mesh sieve, and is subsequently filled in portions of 0.55 g into hard gelatin capsules. The capsule prepared contains doxepine-polymethacrylate corresponding to 200 mg of doxepine base.

EXAMPLE 3

Preparation of sustained release capsules containing chloropromazine 100 g of chloropromazine hydrochloride [10-(3'-methylamino-propyl)-2-chloro-phenothiazine hydrochloride] (USP XX) is dissolved in 1 liter of deionized water and added at constant stirring to a solution of $(NH_4^+)$-polymethacrylate of the following composition:

Copolymer MPM-05 . . . 135 g
30 percent (w/v) aqueous ammonia solution . . . 16 ml
Deionized water . . . 1700 ml The precipitate formed is decanted, filtered, washed, dried and granulated as in Example 2, then the product is filled in portions of 0.187 g into hard gelatin capsules.

The capsule prepared contains chloropromazine-polymethacrylate corresponding to 75 mg of chloropromazine base.

EXAMPLE 4

Preparation of sustained release capsules containing trimipramine 100 g of trimipramine maleate [5-(3-dimethylamino-2-methylpropyl)-10,11-dihydrodibenz[b,f]azepine hydrogen maleate] (BP-1973) is dissolved in 1 liter of deionized water and added with constant stirring to a solution of K-polymethacrylate of the following composition:

Copolymer MPM-06 . . . 146 g
6 percent (w/v) aqueous potassium hydroxide solution . . . 456 ml
Deionized water . . . 800 ml The precipitate formed is decanted, filtered, washed, dried and granulated according to Example 2, then is filled in portions of 0.458 g into hard gelatin capsules.

The capsule prepared contains trimipramine-polymethacrylate corresponding to 150 mg of trimipramine base.

EXAMPLE 5

Preparation of sustained release capsules containing quinidine 100 g of quinidine bisulfate (6-methoxy-α-(5-vinyl-2-quinuclidinyl)-4-quinolinemethanol bisulfate) (Extra Pharmacopoeia Martindale XXVII Ed.) is dissolved in 1.5 liters of deionized water and added at constant stirring to a solution of sodium-polymethacrylate of the following composition:

Copolymer Eudragit L-100 . . . 83 g
6 percent (w/v) aqueous sodium hydroxide solution . . . 275 ml
Deionized water . . . 1300 ml The precipitate formed is decanted, filtered, washed, dried and granulated according to the process of Example 2, and is subsequently filled in portions of 0.354 g into hard gelatin capsules. The capsule prepared contains quinidine-polymethacrylate corresponding to 170 mg of quinidine base.

EXAMPLE 6

Preparation of sustained release capsules containing bencyclane 100 g of bencyclane hydrogenfumarate [1-benzyl-1-(3-dimethylaminopropoxy)cycloheptane hydrogenfumarate] is dispersed in 1 liter of water, 198 ml of 5 percent (w/v) sodium hydroxide solution added and stirred till all solid material is completely dissolved.

2 liters of a 5 percent (w/v) sodium hydroxide solution is poured into 713 ml of a copolymer dispersion containing 30 percent of Eudragit L 30 D. 50 g of microcrystalline cellulose (U.S.N.F.XV) is dispersed into the obtained sodium-polymathacrylate solution, then, at constant stirring, the above bencyclane solution is made to flow into it. The precipitate formed is decanted, filtered, washed, dried and granulated according to the procedure described in Example 2, and is subsequently filled in portions of 0.476 g into hard gelatin capsules. The resulting capsule contains bencyclane-polymethacrylate corresponding to 100 mg of bencyclane base.

EXAMPLE 7

Preparation of sustained release tablets containing papaverine 100 g of papaverine hydrochloride [1-(3,4-dimethoxybenzyl)-6,7-dimethoxyisoquinoline hydrochloride] (USP XX) is dissolved in 1 liter of deionized water and added to a suspension of sodium-polymethacrylate of the following composition:

6 percent (w/w) copolymer dispersion of Eudragit L 30 . . . 1950 g
5 percent (w/v) aqueous sodium hydroxide solution . . . 171 ml Microcrystalline cellulose (U.S.N.F.XV) . . . 22 g The precipitate formed is decanted, filtered, washed, dried and granulated according to Example 2. The granulate is homogenized, together with 20 percent of microcrystalline cellulose (U.S.N.F.XV) and 0.2 percent of magnesium stearate (100 mesh), and the mixture used for pressing tablets of an average weight of 0.5 g (tablet strength: 5.0 to 5.5 kg). The resulting tablet contains papaverine-polymethacrylate corresponding to 100 mg of papaverine base.

EXAMPLE 8

Preparation of sustained release tablets containing chloranolol 100 g of chloranolol hydrochloride [1-(2,5-dichlorophenoxy)-2-hydroxy-3-t-butylaminopropane hydrochloride] is mixed at constant stirring with 1 liter of deionized water and a solution of sodium-polymethacrylate of the following composition:
  6 percent (w/w) aqueous copolymer dispersion of Eudragit L 30 D . . . 3146 g
  5 percent (w/v) aqueous sodium hydroxide solution . . . 235 ml The mixture is stirred continuously for 2 hours, then the resulting precipitate is decanted, filtered, washed, dried and granulated according to the procedure described in Example 2. One part (w) of this granulate is homogenized together with 0.87 parts (w) of lactose (50 mesh, USP XX), the homogenisate humidified with a 20 percent (w/v) aqueous Povidone solution (polyvinylpyrrolidone) (USP XX), granulated on a 20 mesh sieve. The granulate is regranulated on a 25 mesh sieve and subsequently homogenized together with 0.0321 parts (w) (80 mesh) of magnesium stearate.

The mixture is used for pressing tablets of an average weight of 0.125 g (tablet strength: 3 kg). The resulting tablets contain chloranolol-polymethacrylate corresponding to 20 mg of chloranolol base each.

What we claim is:

1. A stable solid pharmaceutical product for the sustained release of a pharmaceutical compound, which is the reaction product of a water soluble salt of a pharmaceutically active compound containing a secondary or tertiary amino group and an alkali or ammonium salt of an acid-group-containing synthetic copolymer selected from the group consisting of 1:1 mole ratio methacrylic acid/methacrylic acid methyl ester, 1:1 mole ratio methacrylic acid/acrylic acid methyl ester and 1:1:1 mole ratio methacrylic acid/acrylic acid methyl ester/methacrylic acid methyl ester copolymers.

2. A stable solid pharmaceutical product for the sustained release of a pharmaceutically active compound, which is a reaction product of a pharmaceutically active compound selected from the group consisting of beta-phenyl-propanol-methylamine hydrochloride, 11(3-dimethylamine-propylidane)-6,11-dihydro-dibenzo[b,e]oxepine hydrochloride, 10-(3'-methylamino-propyl)-2-chloro-phanothiazine hydrochloride, 5-(3-dimethylamino-2-methyl-propyl)-10,11-dihydro-benz[b,f]azepine hydrogenmaleate, 6-methoxy-$\alpha$-(5-vinyl-2-quinuclidinyl)-4-quinolinemethanole-bisulfate, 1-benzyl-1-(3-dimethylaminopropoxy)cycloheptane hydrogenfumarate, 1-(3,4-dimethoxybenzyl)-6,7-dimethoxyisoquinoline hydrochloride, 1-(2,5-dichlorophenoxy)-2-hydroxy-3-t-butylaminopropane hydrochloride and an alkali or ammonium salt of an acid-group-containing synthetic copolymer selected from the group consisting of 1:1 mole ratio methacrylic acid/methacrylic acid methyl ester, 1:1 mole ratio methacrylic acid/acrylic acid methyl ester and 1:1:1 mole ratio methacrylic acid/acrylic acid methyl ester/methacrylic acid methyl ester copolymers.

3. A sustained release pharmaceutical product, which is the reaction product of 11-(3-dimethylaminopropylidene)-6,11-dihydro-dibenzo(b,e)oxepine hydrochloride and the sodium salt of 1:1 mole ratio methacrylic acid/methacrylic acid methyl ester copolymer.

4. A sustained release pharmaceutical product, which is the reaction product of 5-(3-dimethylamino-2-methylpropyl)-10,11-dihydro-benz(b,f)azepine hydrogen maleate and the potassium salt of 1:1:1 mole ratio methacrylic acid/acrylic acid methyl ester/methacrylic acid methyl ester copolymer.

5. A sustained release pharmaceutical product, which is the reaction product of 6-methoxy-$\alpha$-(5-vinyl-2-quinuclidinyl)-4-quinoline-methanol bisulfate and the sodium salt of 1:1 mole ratio methacrylic acid/methacrylic acid methyl ester copolymer.

6. A sustained release pharmaceutical product, which is the reaction product of 1-benzyl-1-(3-dimethylaminopropoxy)-cycloheptane hydrogenfumarate and the sodium salt of 1:1 mole ratio methacrylic acid/methacrylic acid methyl ester copolymer.

7. A sustained release pharmaceutical product which is the reaction product of 1-(3,4-dimethoxybenzyl)-6,7-dimethoxyisoquinoline hydrochloride and the sodium salt of 1:1 mole ratio methacrylic acid/methacrylic acid methyl ester copolymer.

* * * * *